United States Patent
Lehtonen

(12) 
(10) Patent No.: US 6,462,045 B1
(45) Date of Patent: Oct. 8, 2002

(54) METHOD OF TREATING PULMONARY HYPERTENSION

(75) Inventor: Lasse Lehtonen, Espoo (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/720,198

(22) PCT Filed: Jun. 18, 1999

(86) PCT No.: PCT/FI99/00540

§ 371 (c)(1),
(2), (4) Date: Feb. 22, 2001

(87) PCT Pub. No.: WO99/66912

PCT Pub. Date: Dec. 29, 1999

(30) Foreign Application Priority Data

Jun. 25, 1998 (FI) .................................. 981473

(51) Int. Cl.⁷ .............................................. A61K 31/50
(52) U.S. Cl. ...................................................... 514/247
(58) Field of Search ........................................ 514/247

(56) References Cited

FOREIGN PATENT DOCUMENTS

| EP | 579 260 | * | 1/1994 |
| WO | 92/12135 | * | 7/1992 |
| WO | 93-21921 | | 11/1993 |

OTHER PUBLICATIONS

Lilleberg et al, Eu. Heart J., 1998, 19, 660–668.*
Fishman, "Epoprostenal (Prostacyclin) and Pulmonary Hypertension", Editorial, Annals of Internal Medicine, vol. 132, No. 6, pp. 500–502 (2000).

Sundberg et al., "Hemodynamic and Neurohumoral Effects of Levosimendan, a New Calcium Sensitizer, at Rest and During Exercise in Healty Men", Am. J. Cardiol, vol. 75, pp. 1061–1066 (1995).

Sandell et al., "Pharmacokinetics of Levosimendan in Healthy Volunteers and Patients with Congestive Heart Failure", J. Cardio. Pharm., vol. 26, suppl. 1, pp. S57–S62 (1995).

Lehtonen et al., "Safety of Levosimendan and Other Calcium Sensitizers", J. Cardio. Pharm., vol. 26, supp. 1, pp. S70–S76 (1995).

Lilleberg et al., "Dose–Range Study of a New Calcium Sensitizer, Levosimendan, in Patients with Left Ventricular Dysfunction", J. Cardio. Pharm., vol. 26, supp. 1, pp. S63–S69 (1995).

Butt, "Pathophysiological; basis of the treatment of pulmonary hypertension", Eur. Respir. Rev., vol. 5:29, pp. 248–251 (1995).

* cited by examiner

*Primary Examiner*—Rebecca Cook
(74) *Attorney, Agent, or Firm*—Finnegan, Henderson, Farabow, Garrett & Dunner, L.L.P.

(57) ABSTRACT

Levosimendan, or (−)-[[4-(1,4,5,6-tetrahydro-4-methyl-6-oxo-3-pyridazinyl)phenyl]hydrazono]-propanedinitrile, which has been previously suggested for tho treatment of congestive heart failure is useful in the treatment of pulmonary hypertension.

1 Claim, 1 Drawing Sheet

METHOD OF TREATING PULMONARY HYPERTENSION

This application is a national stage filing of PCT International Application No. PCT/FI99/00540, filed on Jun. 18, 1999, which published in the English language.

TECHNICAL FIELD

The present invention relates to the use of levosimendan, or (−)-[[4-(1,4,5,6-tetrahydro-4-methyl-6-oxo-3-pyridazinyl)phenyl]hydrazono]propanedinitrile (I), or pharmaceutically acceptable salts thereof in the manufacture of a medicament for the treatment of pulmonary hypertension.

BACKGROUND OF THE INVENTION

Levosimendan, which is the (−)-enantiomer of [[4-(1,4,5,6-tetrahydro-4-methyl-6-oxo-3-pyridazinyl)phenyl]hydrazono]propanedinitrile, and the method for its preparation is described in EP 565546 B1. Levosimendan is potent in the treatment of heart failure and has significant calcium dependent binding to troponin. Levosimendan is represented by the formula:

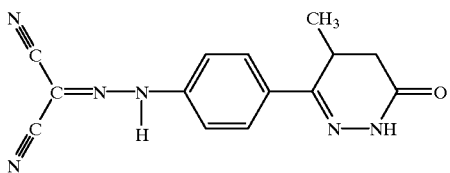

I

The hemodynamic effects of levosimendan in man are described in Sundberg, S. et al., Am. J. Cardiol., 1995; 75: 1061–1066 and in Lilleberg, J. et al., J. Cardiovasc. Pharmacol., 26(Suppl.1), S63–S69, 1995. Pharmacokinetics of levosimendan in man after i.v. and oral dosing is described in Sandell, E.-P. et al., J. Cardiovasc. Pharmacol., 26(Suppl.1), S57–S62, 1995. The use of levosimendan in the treatment of myocardial ischemia is described in WO 93/21921. Clinical studies have confirmed the beneficial effects of levosimendan in heart failure patients.

Pulmonary hypertension is classified clinically as either primary of secondary. Primary pulmonary hypertension, the cause of which is as yet unknown, is diagnosed only after all secondary causes, such as pulmonary emboli, of increased pulmonary pressure are excluded.

At the moment there is no successful cure for pulmonary hypertension. Administration of vasodilatating drugs has not proved to be useful in patients suffering from pulmonary hypertension. The prognosis is poor, with a median survival time of about 2 years.

SUMMARY OF THE INVENTION

It has now been found that levosimendan is useful in the treatment of pulmonary hypertension.

Therefore, the present invention provides the use of (−)-[[4-(1,4,5,6-tetra-hydro-4-methyl-6-oxo-3-pyridazinyl)phenyl]hydrazono]propanedinitrile or a pharmaceutically acceptable salt thereof in the manufacture of a medicament for the treatment of pulmonary hypertension.

The present invention also provides a method for the treatment of pulmonary hypertension in a patient, said method comprising administering to a patient in need thereof a pulmonary blood pressure lowering amount of (−)-[[4-(1,4,5,6-tetrahydro-4-methyl-6-oxo-3-pyridazinyl)phenyl]hydrazono]propanedinitrile or a pharmaceutically acceptable salt thereof.

DETAILED DESCRIPTION

Figure 1:
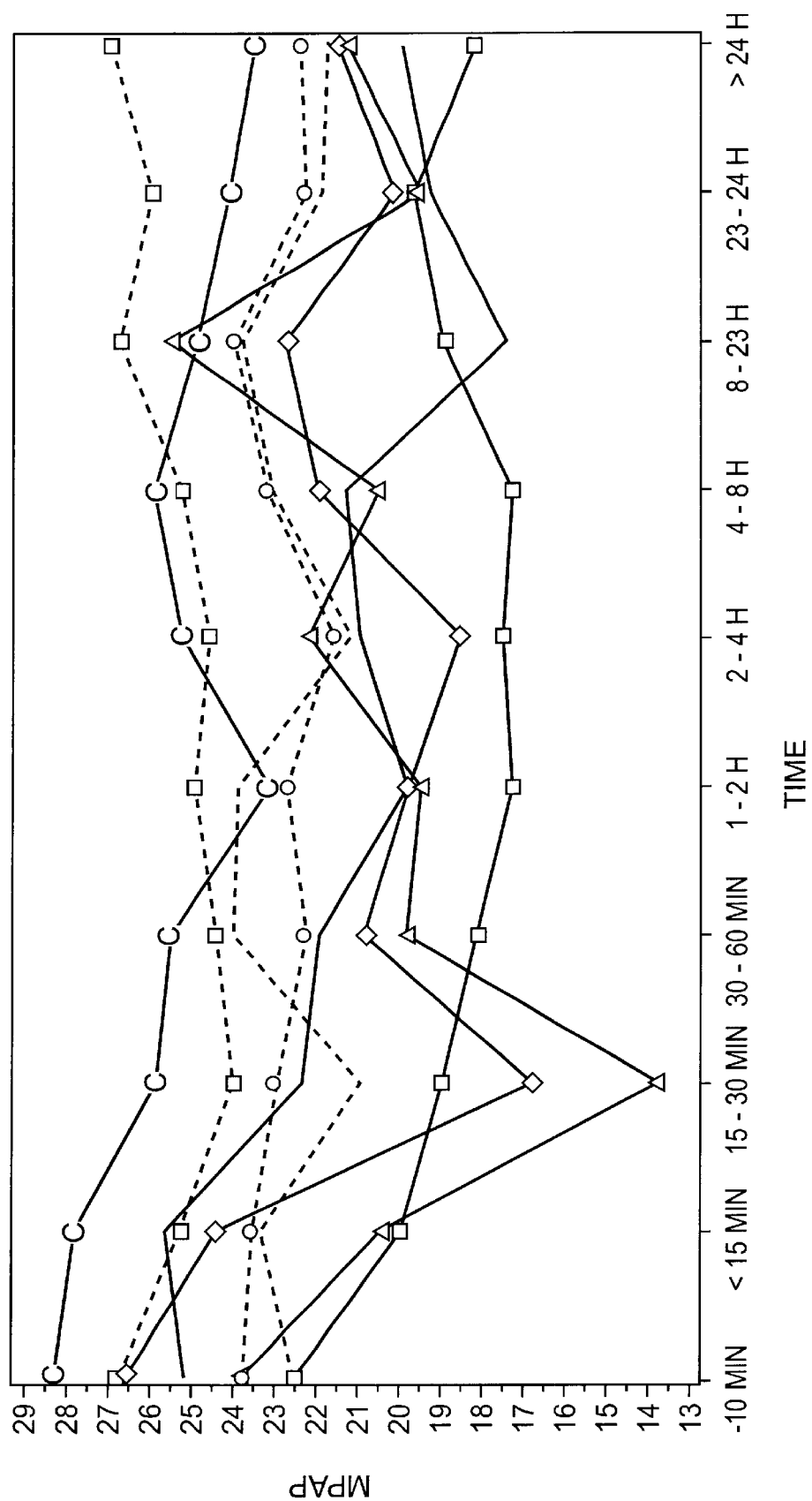
FIG. 1 shows the change in the mean pulmonary artery pressure after administering of levosimendan by infusion for 24 hours.

Levosimendan is formulated into dosage forms suitable for the treatment of pulmonary hypertension using the principles known in the art. It is given to mammalian organisms, e.g. humans, as such or in combination with suitable pharmaceutical excipients in the form of tablets, dragees, capsules, suppositories, emulsions, suspensions or solutions whereby the contents of the active compound in the formulation is from about 0.5 to 100% per weight. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds, release controlling components and other ingredients normally used in this field of technology may be also used.

For oral administration in tablet form, suitable carriers and excipients include e.g. lactose, corn starch, magnesium stearate, calcium phosphate and talc. For oral administration in capsule form, useful carriers and excipients include e.g. lactose, corn starch, magnesium stearate and talc. For controlled release oral compositions release controlling components can be used. Typical release controlling components include hydrophilic gel forming polymers such as hydroxypropylmethyl cellulose, hydroxypropyl cellulose, carboxymethyl celluloses, alginic acid or a mixture thereof; vegetable fats and oils including vegetable solid oils such as hydrogenated soybean oil, hardened castor oil or castor seed oil (sold under trade name Cutina HR), cotton seed oil (sold under the trade names Sterotex or Lubritab) or a mixture thereof; fatty acid esters such as triglycerides of saturated fatty acids or their mixtures e.g. glyceryl tristearates, glyceryl tripalmitates, glyceryl trimyristates, glyceryl tribehenates (sold under the trade name Compritol) and glyceryl palmitostearic acid ester.

Tablets can be prepared by mixing the active ingredient with the carriers and excipients and compressing the powdery mixture into tablets. Capsules can be prepared by mixing the active ingredient with the carriers and excipients and placing the powdery mixture in capsules, e.g. hard gelatin capsules. Formulations suitable for intravenous administration comprise sterile isotonic solutions of levosimendan and vehicle, preferably aqueous solutions.

The method of the invention comprises a step of administering to a subject an amount of levosimendan effective to lower the pulmonary blood pressure of the subject. The administration can be effected enterally, e.g. orally or rectally or parenterally, e.g. intravenously or transdermal. A therapeutically effective amount of levosimendan to be administered to a subject depends upon the condition to be treated, the route of administration, age, weight and the condition of the patient. In general levosimendan is administered orally to man in doses from about 0.1 to 20 mg, preferably from 0.2 to 10 mg, more preferably from 0.5 to 5 mg once or several times a day depending on the age, body weight and condition of the patient. Levosimendan can be administered intravenously with the infusion rate in the range of about 0.005 to 100 μg/kg/min, typically 0.01 to 20 μg/kg/min, preferably about 0.02 to 10 μg/kg/min.

Salts of levosimendan may be prepared by known methods. Pharmaceutically acceptable salts are useful as active medicaments, however, preferred salts are the salts with alkali or alkaline earth metals.

EXAMPLES

Experiment 1

Levosimendan (LS) was administered by infusion (0.05–0.6 μg /kg/min) to totally 95 patients (n=14–23 per group) in amounts of 0.05, 0.1, 0.2, 0.4 and 0.6 μg/kg/min for 24 hrs. The change in the mean pulmonary artery pressure was determined. The results are shown in FIG. 1, wherein ------ is placebo, --O-- is vehicle, --□-- is dobutamine,
— is LS 0.05 μg/kg/min, —C— is LS 0.1 μg/kg/min,
—□— is LS 0.2 μg/kg/min,
—◇— is LS 0.4 μg/kg/min, —Δ— is LS 0.6 μg/kg/min The results show that levosimendan (LS) was able to significantly lower pulmonary artery pressure.

Experiment 2

Levosimendan was administered by infusion (0.1–0.4 μg/kg/min) to a patient with pulmonary hypertension in amounts of 0.1, 0.2 and 0.4 μg/kg/min for 5.5 hrs. At 0.25 h the infusion rate was 0.1 μg/kg/min, at 2.00 h the infusion rate was increased to 0.2 μg/kg/min and at 4.5 h the infusion rate was increased to 0.4 μg/kg/min. The change in the mean pulmonary artery pressure (MPAP) was determined. The results are shown in Table 1. The results show that levosimendan (LS) was able to significantly lower pulmonary artery pressure.

Table 1. The change of mean pulmonary artery pressure (NPAP) during levosimendan infusion. 0.25 h infusion rate 0.1 μg/kg/min, 2.00 h infusion rate 0.2 μg/kg/min, 4.5 h infusion rate 0.4 μg/kg/min.

| Time (h) | MPAP (mmHg) |
|---|---|
| 0 | 41 |
| 0.75 | 42 |
| 1.25 | 42 |
| 1.75 | 39 |
| 2.50 | 34 |
| 3.00 | 35 |
| 3.50 | 35 |
| 4.00 | 32 |
| 5.00 | 27 |
| 5.50 | 29 |

Pharmaceutical Example 1

| Hard gelatin capsule size 3 | |
|---|---|
| Levosimendan | 2.0 mg |
| Lactose | 198 mg |

The pharmaceutical preparation in the form of a capsule was prepared by mixing levosimendan with lactose and placing the powdery mixture in hard gelatin capsule.

What is claimed is:

1. A method for the treatment of pulmonary hypertension in a patient, said method comprising administering to the patient in need thereof a pulmonary blood pressure lowering amount of (−)-[[4-(1,4,5,6-tetrahydro-4-methyl-6-oxo-3-pyridazinyl)phenyl]hydrazono]propanedinitrile or a pharmaceutically acceptable salt thereof.

* * * * *